US012285266B2

United States Patent
Mazumder et al.

(10) Patent No.: US 12,285,266 B2
(45) Date of Patent: Apr. 29, 2025

(54) METHOD AND SYSTEM FOR DETERMINING MYOCARDIAL ISCHEMIA SEVERITY BASED ON HEMODYNAMIC PARAMETERS ESTIMATION

(71) Applicant: Tata Consultancy Services Limited, Mumbai (IN)

(72) Inventors: Oishee Mazumder, Kolkata (IN); Dibyendu Roy, Kolkata (IN); Aniruddha Sinha, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 426 days.

(21) Appl. No.: 17/445,292

(22) Filed: Aug. 17, 2021

(65) Prior Publication Data

US 2022/0104763 A1 Apr. 7, 2022

(30) Foreign Application Priority Data

Aug. 21, 2020 (IN) .............................. 202021036165

(51) Int. Cl.
*A61B 5/00* (2006.01)
*A61B 5/02* (2006.01)
(Continued)

(52) U.S. Cl.
CPC ........ *A61B 5/4842* (2013.01); *A61B 5/02007* (2013.01); *A61B 5/021* (2013.01);
(Continued)

(58) Field of Classification Search
CPC ................................ A61B 5/4842; A61B 5/36
(Continued)

(56) References Cited

U.S. PATENT DOCUMENTS

| RE39,897 E | 10/2007 | Mower | |
|---|---|---|---|
| 2006/0167359 A1* | 7/2006 | Bennett | A61B 5/29 600/485 |
| 2011/0054557 A1* | 3/2011 | Yu | A61N 1/365 607/19 |

OTHER PUBLICATIONS

Elham Kayvanpour et al., "Towards Personalized Cardiology: Multi-Scale Modeling of the Failing Heart", Applied Bionics and Biomechanics, Aug. 2015, vol. 10(7), PLOS one, https://www.researchgate.net/publication/281817815_Towards_Personalized_Cardiology_Multi-Scale_Modeling_of_the_Failing_Heart/link/5677c9f708ae125516ee3c5a/download.

(Continued)

*Primary Examiner* — Nicole F Lavert
(74) *Attorney, Agent, or Firm* — FINNEGAN, HENDERSON, FARABOW, GARRETT & DUNNER LLP

(57) ABSTRACT

This disclosure relates generally to method and system for determining myocardial ischemia severity based on hemodynamic parameters estimation. Many patients suffer from myocardial ischemia due to narrowing of coronary artery resulting poor oxygen supply in cardiac muscles. The method includes receiving Electrophysiology (EP) signal from a simulated heart surface model to generate a single lead ECG template. The method further estimates hemodynamic parameters using a hemodynamic module based on the single lead ECG template and then estimates cardiac pressure-volume loop variables. The myocardial ischemia severity of the heart surface model is determined which includes one of moderate ischemia, severe ischemia and silent ischemia. Here, the cardiac source module is coupled with the hemodynamic module to determine cardiac transmembrane potential (TMP) of the heart surface model through contractility function. This method serves as a guidance platform for patient care such as synthetic data (Continued)

generation for disease classification pertaining to coronary artery.

7 Claims, 11 Drawing Sheets

(51) Int. Cl.
    *A61B 5/021*     (2006.01)
    *A61B 5/36*     (2021.01)
    *A61B 5/366*     (2021.01)
    *A61B 5/367*     (2021.01)

(52) U.S. Cl.
    CPC ................ *A61B 5/36* (2021.01); *A61B 5/366* (2021.01); *A61B 5/367* (2021.01)

(58) Field of Classification Search
    USPC ........................................................ 600/513
    See application file for complete search history.

(56) References Cited

OTHER PUBLICATIONS

Anniek F. Lubberding et al., "Comparison of hemodynamics, cardiac electrophysiology and ventricular arrhythmia in an open and a closed chest porcine model of acute myocardial infarction Title of the item: Translational Physiology", Feb. 2020, vol. 318(2), NCBI, https://journals.physiology.org/doi/pdf/10.1152/ajpheart.00406.2019.

\* cited by examiner

Cardiac and Torso potential at ventricular systole, t= 220 ms;

Cardiac and Torso potential at ventricular diastole, t= 440 ms;

METHOD AND SYSTEM FOR DETERMINING MYOCARDIAL ISCHEMIA SEVERITY BASED ON HEMODYNAMIC PARAMETERS ESTIMATION

PRIORITY CLAIM

This U.S. patent application claims priority under 35 U.S.C § 119 to Indian patent application no. (202021036165), filed on Aug. 21, 2020. The entire contents of the aforementioned application are incorporated herein by reference.

TECHNICAL FIELD

The disclosure herein generally relates to myocardial ischemia disease, and, more particularly, to method and system for determining myocardial ischemia severity based on hemodynamic parameters estimation.

BACKGROUND

Myocardial ischemia leads to sudden cardiac death due to narrowing of coronary artery causing poor oxygen deprivation in cardiac muscles. Many patients suffer from myocardial ischemia due to smoking, diabetes, hypertension, and the like. Early detection of myocardial ischemia provides opportunity for a wide range of effective therapies such as surgical revascularization, neural stimulation, and drug delivery to reduce cardiac workload or to improve cardiac circulation. In recent years, computer simulations and mathematical models have provided substantial insights for electrophysiological behavior to detect abnormalities in myocardial ischemia. Varying ischemia conditions in cardiac contractility results inefficient pumping in heart muscles and thus hampers hemodynamic equilibrium. Further, any computer models to determine ischemic progression provides dual effect of change in electrophysiology and hemodynamics as the disease manifests. Concurrently, there have been numerous researches to unravel the progression and manifestation of acute ischemia, but the complexity of induced changes in ischemia have inaccurate evaluation and alteration of cardiac properties with progression of the disease. In such scenarios, a scalable and performance efficient technique is necessary for assessing the progression of myocardial ischemia by observing the change in disease severity.

Conventionally, myocardial ischemia has been detected by analyzing the recorded electrocardiogram (ECG) signals from the body surface using amplifiers and associated instrumentation. To monitor patients for ischemia and myocardial infarction, physicians rely upon periodic ECG signals which generally require as many as ten leads to be attached to the patient. In addition, physicians generally require the patient to take a stress test wherein the patient perform activity such as walking/running on a treadmill until the patient is essentially exhausted to stress the heart. Such methods may lack ability to efficiently deal with large numbers of mixed scenarios due to varying change in cardiac contractility. Also, several open source platforms enabled computer simulations and mathematical models to determine ischemic progression such as SCIRun problem solving environment. These open source platforms lack in the fact that they process only the underlying electrophysiology signals, neglecting the effect of ischemic progression in cardiac hemodynamic.

SUMMARY

Embodiments of the present disclosure present technological improvements as solutions to one or more of the above-mentioned technical problems recognized by the inventors in conventional systems. For example, in one embodiment, a method for determining myocardial ischemia severity based on hemodynamic parameter estimation is provided. The system includes for determining myocardial ischemia severity based on hemodynamic parameter estimation is provided. The method includes receiving a plurality of Electrophysiology (EP) signals from a heart surface model as an input. Each Electrophysiology (EP) signal from the plurality of Electrophysiology (EP) signals corresponds to cardiac transmembrane potential (TMP) giving rise to cardiac contraction. Further, a Forward Electrophysiology signal from the plurality of Electrophysiology (EP) signals is generated by a cardiac source module. Further, the Forward Electrophysiology signal are processed to generate a single lead ECG template, wherein the single lead ECG template comprises at least one parameter comprising: (i) a auricular depolarization (PQ) segment, (ii) a ventricular depolarization (QRS) segment, (iii) a ventricular repolarization (ST) segment and combination thereof. Further, using a hemodynamic module, a plurality of hemodynamic parameters based on the single lead ECG template is estimated. The plurality of hemodynamic parameters comprises a left heart atrium compliance function $C_{la}(t)$ and a left heart ventricle compliance function $C_{lv}(t)$. Then, a plurality of cardiac pressure-volume loop variables is estimated based on at least one of (i) the plurality of hemodynamic parameters, and (ii) pressure variation associated with cardiac excitation. Furthermore, myocardial ischemia severity of the heart surface model is determined based on at least one of (i) a scar tissue size, (ii) a velocity reduction value of the cardiac affected region, (iii) the transmembrane potential (TMP) amplitude and repolarization time, (iv) the single lead ECG template and (v) the plurality of cardiac pressure-volume loop variables. The myocardial ischemia severity includes one of moderate ischemia, severe ischemia and silent ischemia.

Further, the system of the cardiac source module is coupled with the hemodynamic module to determine cardiac transmembrane potential (TMP) of the heart surface model through a contractility function. The left heart atrium compliance function $C_{la}(t)$ is computed based on at least one of (i) a minimum value of the left heart atrium, (ii) a maximum value of the left heart atrium, (iii) a left heart atrium activation function $(A_{la})$, and (iv) a time delay in firing between the left heart atrium and the left heart ventricle. Further, the left heart atrium activation function $(A_{la})$ is computed based on left heart atrium activation time analogous to the auricular depolarization (PQ) segment and the time duration of the cardiac cycle. The left heart ventricle compliance function $C_{lv}(t)$ is computed based on the end systolic compliance and the left heart ventricle activation function $(A_{lv}(t))$. The left heart ventricle activation function $(A_{lv}(t))$ is computed based on an end systolic and diastolic time duration of the cardiac cycle analogous to (i) the ventricular depolarization (QRS) segment, and (ii) the ventricular repolarization (ST) segment. The plurality of cardiac pressure-volume loop variables includes at least one of (i) a dynamic change observed in a systemic artery pressure, (ii) a dynamic change observed in a left heart ventricle pressure and (iii) a dynamic change observed in a right ventricle pressure. Further, the dynamic change observed in the systemic artery pressure is estimated based on at least one of (i) a systemic artery compliance, (ii) the left heart ventricle pressure, (iii) a systemic ventricle pressure, (iv) a systemic artery pressure, (v) a resistance value observed in systemic vessels, and (vi) a resistance value observed in aortic vessel.

The dynamic change observed in the left heart ventricle pressure is estimated based on at least one of (i) the left heart ventricle compliance function, (ii) the left heart ventricle pressure, (iii) a pulmonary vein pressure, (iv) the systemic artery pressure, (v) a resistance value observed in mitral vessel, and (vi) the resistance value observed in aortic vessel. The dynamic change observed in the right heart ventricle pressure is estimated based on at least one of (i) the right heart ventricle compliance function, (ii) a systemic vein pressure (iii) the right heart ventricle pressure, (iv) a resistance value observed in tricuspid vessel, (v) a pulmonary artery pressure, and (vi) a resistance value observed in pulmonary valve.

The moderate myocardial ischemia is determined if (i) the scar tissue size varies between a first threshold value and a second threshold value, (ii) the velocity reduction value of cardiac affected region is equal to a velocity value, and (iii) the cardiac transmembrane potential (TMP) amplitude and repolarization time range between a first repolarization time value and a second repolarization time value. The severe myocardial ischemia is determined if (i) the scar tissue size varies between a first predetermined value and a second predetermined value, (ii) the velocity reduction value of cardiac affected region is equal to a velocity value, and (iii) the cardiac transmembrane potential (TMP) amplitude and repolarization time range between a first transmembrane potential amplitude value and a second transmembrane potential amplitude value. The silent myocardial ischemia is determined if (i) the scar tissue size varies between a first predefined value and a second predefined value, (ii) the velocity reduction value of cardiac affected region is equal to a velocity value, and (iii) the cardiac transmembrane potential (TMP) amplitude and repolarization time range between a first transmembrane potential value and a second transmembrane potential value.

In another aspect, a method for determining myocardial ischemia severity based on hemodynamic parameter estimation is provided. The method includes receiving a plurality of Electrophysiology (EP) signals from a heart surface model as an input. Each Electrophysiology (EP) signal from the plurality of Electrophysiology (EP) signals corresponds to cardiac transmembrane potential (TMP) giving rise to cardiac contraction. Further, a Forward Electrophysiology signal from the plurality of Electrophysiology (EP) signals is generated by a cardiac source module. Further, the Forward Electrophysiology signal are processed to generate a single lead ECG template, wherein the single lead ECG template comprises at least one parameter comprising: (i) a auricular depolarization (PQ) segment, (ii) a ventricular depolarization (QRS) segment, (iii) a ventricular repolarization (ST) segment and combination thereof. Further, using a hemodynamic module, a plurality of hemodynamic parameters based on the single lead ECG template is estimated. The plurality of hemodynamic parameters comprises a left heart atrium compliance function $C_{la}(t)$ and a left heart ventricle compliance function $C_{lv}(t)$. Then, a plurality of cardiac pressure-volume loop variables is estimated based on at least one of (i) the plurality of hemodynamic parameters, and (ii) pressure variation associated with cardiac excitation. Furthermore, myocardial ischemia severity of the heart surface model is determined based on at least one of (i) a scar tissue size, (ii) a velocity reduction value of the cardiac affected region, (iii) the transmembrane potential (TMP) amplitude and repolarization time, (iv) the single lead ECG template and (v) the plurality of cardiac pressure-volume loop variables. The myocardial ischemia severity includes one of moderate ischemia, severe ischemia and silent ischemia.

Further, the method of the cardiac source module is coupled with the hemodynamic module to determine cardiac transmembrane potential (TMP) of the heart surface model through contractility function. The left heart atrium compliance function $C_{la}(t)$ is computed based on at least one of (i) a minimum value of the left heart atrium, (ii) a maximum value of the left heart atrium, (iii) a left heart atrium activation function ($A_{la}$), and (iv) a time delay in firing between the left heart atrium and the left heart ventricle. Further, the left heart atrium activation function ($A_{la}$) is computed based on the left heart atrium activation time analogous to the auricular depolarization (PQ) segment and the time duration of the cardiac cycle. The left heart ventricle compliance function $C_{lv}(t)$ is computed based on the end systolic compliance and the left heart ventricle activation function ($A_{lv}(t)$). The left heart ventricle activation function ($A_{lv}(t)$) is computed based on systolic and diastolic time duration of the cardiac cycle analogous to (i) the ventricular depolarization (QRS) segment, and (ii) the ventricular repolarization (ST) segment. The plurality of cardiac pressure-volume loop variables includes at least one of (i) a dynamic change observed in a systemic artery pressure, (ii) a dynamic change observed in a left heart ventricle pressure and (iii) a dynamic change observed in a right ventricle pressure. Further, the dynamic change observed in the systemic artery pressure is estimated based on at least one of (i) left heart ventricle pressure is estimated based on at least one of (i) the left heart ventricle compliance function, (ii) the left heart ventricle pressure, (iii) a pulmonary vein pressure, (iv) the systemic artery pressure, (v) a resistance value observed in mitral vessel, and (vi) the resistance value observed in aortic vessel. The dynamic change observed in the right heart ventricle pressure is estimated based on at least one of (i) the right heart ventricle compliance function, (ii) a systemic vein pressure (iii) the right heart ventricle pressure, (iv) a resistance value observed in tricuspid vessel, (v) a pulmonary artery pressure, and (vi) a resistance value observed in pulmonary valve.

The moderate myocardial ischemia is determined if (i) the scar tissue size varies between a first threshold value and a second threshold value, (ii) the velocity reduction value of cardiac affected region is equal to a velocity value, and (iii) the cardiac transmembrane potential (TMP) amplitude and repolarization time range between a first repolarization time value and a second repolarization time value. The severe myocardial ischemia is determined if (i) the scar tissue size varies between a first predetermined value and a second predetermined value, (ii) the velocity reduction value of cardiac affected region is equal to a velocity value, and (iii) the cardiac transmembrane potential (TMP) amplitude and repolarization time range between a first transmembrane potential amplitude value and a second transmembrane potential amplitude value. The silent myocardial ischemia is determined if (i) the scar tissue size varies between a first predefined value and a second predefined value, (ii) the velocity reduction value of cardiac affected region is equal to a velocity value, and (iii) the cardiac transmembrane potential (TMP) amplitude and repolarization time range between a first transmembrane potential value and a second transmembrane potential value.

In yet another aspect, provides one or more non-transitory machine readable information storage mediums comprising one or more instructions, which when executed by one or more hardware processors perform actions includes receiving a plurality of Electrophysiology (EP) signals from a heart surface model as an input. Each Electrophysiology (EP) signal from the plurality of Electrophysiology (EP) signals corresponds to cardiac transmembrane potential (TMP) giving rise to cardiac contraction. Further, a Forward Electrophysiology signal from the plurality of Electrophysiology (EP) signals is generated by a cardiac source module. Further, the Forward Electrophysiology signal are processed to generate a single lead ECG template, wherein the single lead ECG template comprises at least one parameter comprising: (i) a auricular depolarization (PQ) segment, (ii) a ventricular depolarization (QRS) segment, (iii) a ventricular repolarization (ST) segment and combination thereof. Further, using a hemodynamic module, a plurality of hemodynamic parameters based on the single lead ECG template is estimated. The plurality of hemodynamic parameters comprises a left heart atrium compliance function $C_{la}(t)$ and a left heart ventricle compliance function $C_{lv}(t)$. Then, a plurality of cardiac pressure-volume loop variables is estimated based on at least one of (i) the plurality of hemodynamic parameters, and (ii) pressure variation associated with cardiac excitation. Furthermore, myocardial ischemia severity of the heart surface model is determined based on at least one of (i) a scar tissue size, (ii) a velocity reduction value of the cardiac affected region, (iii) the transmembrane potential (TMP) amplitude and repolarization time, (iv) the single lead ECG template and (v) the plurality of cardiac pressure-volume loop variables. The myocardial ischemia severity includes one of moderate ischemia, severe ischemia and silent ischemia.

Further, the method of the cardiac source module is coupled with the hemodynamic module to determine cardiac transmembrane potential (TMP) of the heart surface model through contractility function. The left heart atrium compliance function $C_{la}(t)$ is computed based on at least one of (i) a minimum value of the left heart atrium, (ii) a maximum value of the left heart atrium, (iii) a left heart atrium activation function ($A_{la}$), and (iv) a time delay in firing between the left heart atrium and the left heart ventricle. Further, the left heart atrium activation function ($A_{la}$) is computed based on the left heart atrium activation time analogous to the auricular depolarization (PQ) segment and the time duration of the cardiac cycle. The left heart ventricle compliance function $C_{lv}(t)$ is computed based on the end systolic compliance and the left heart ventricle activation function ($A_{lv}(t)$). The left heart ventricle activation function ($A_{lv}(t)$) is computed based on systolic and diastolic time duration of the cardiac cycle analogous to (i) the ventricular depolarization (QRS) segment, and (ii) the ventricular repolarization (ST) segment. The plurality of cardiac pressure-volume loop variables includes at least one of (i) a dynamic change observed in a systemic artery pressure, (ii) a dynamic change observed in a left heart ventricle pressure and (iii) a dynamic change observed in a right ventricle pressure. Further, the dynamic change observed in the systemic artery pressure is estimated based on at least one of (i) left heart ventricle pressure is estimated based on at least one of (i) the left heart ventricle compliance function, (ii) the left heart ventricle pressure, (iii) a pulmonary vein pressure, (iv) the systemic artery pressure, (v) a resistance value observed in mitral vessel, and (vi) the resistance value observed in aortic vessel. The dynamic change observed in the right heart ventricle pressure is estimated based on at least one of (i) the right heart ventricle compliance function, (ii) a systemic vein pressure (iii) the right heart ventricle pressure, (iv) a resistance value observed in tricuspid vessel, (v) a pulmonary artery pressure, and (vi) a resistance value observed in pulmonary valve.

The moderate myocardial ischemia is determined if (i) the scar tissue size varies between a first threshold value and a second threshold value, (ii) the velocity reduction value of cardiac affected region is equal to a velocity value, and (iii) the cardiac transmembrane potential (TMP) amplitude and repolarization time range between a first repolarization time value and a second repolarization time value. The severe myocardial ischemia is determined if (i) the scar tissue size varies between a first predetermined value and a second predetermined value, (ii) the velocity reduction value of cardiac affected region is equal to a velocity value, and (iii) the cardiac transmembrane potential (TMP) amplitude and repolarization time range between a first transmembrane potential amplitude value and a second transmembrane potential amplitude value. The silent myocardial ischemia is determined if (i) the scar tissue size varies between a first predefined value and a second predefined value, (ii) the velocity reduction value of cardiac affected region is equal to a velocity value, and (iii) the cardiac transmembrane potential (TMP) amplitude and repolarization time range between a first transmembrane potential value and a second transmembrane potential value.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Figure 1:
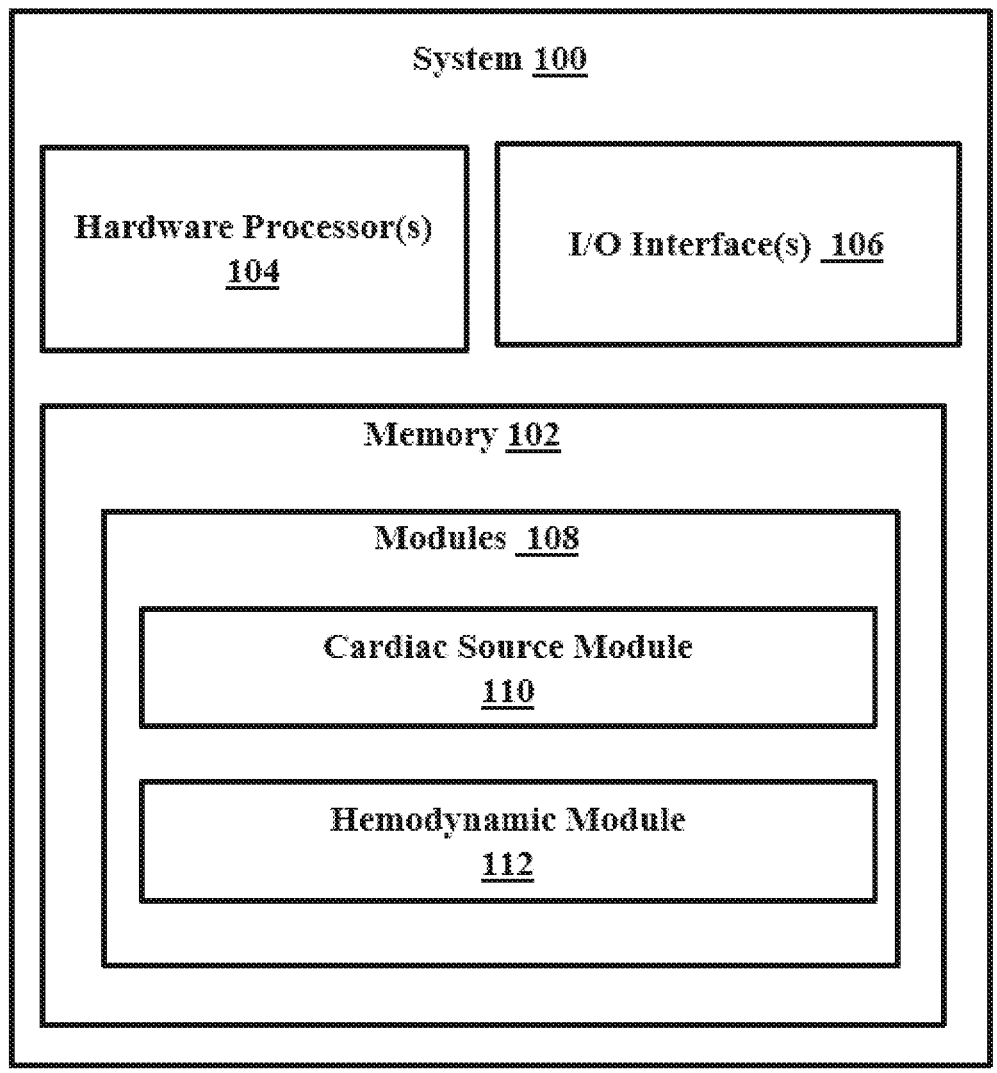
FIG. 1 illustrates an exemplary block diagram of a system for determining myocardial ischemia severity based on hemodynamic parameters estimation, in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Embodiments herein provide a method and system for determining myocardial ischemia severity based on hemodynamic parameters estimation. The method disclosed, enables assessing progression of myocardial ischemic severity based on change occurred in cardiac ejection fraction. The present disclosure is a multi-model simulation of myocardial ischemia to assess disease progression with change in ischemic size and myocardial electrical propagation by observing the changes in hemodynamic parameters. The cardiac multi-model is coupling of a cardiac source model with a hemodynamic module to determine cardiac action transmembrane potential (TMP) of the heart surface model through contractility function. Further, the cardiac disease has a high variable manifestation due to difference in location and extent of damaged area, thus hampering the understanding of disease progression and stratification. Varying myocardial ischemia conditions are assessed based on the morphological changes occurred in a ventricular repolarization (ST) segment of the ECG template. Additionally, the present disclosure provides the assessment of disease progression based on various parameters such as ejection fraction, contractility, blood pressure and thereof for ischemic manifestation which leads to cardiac or heart failure. Three different conditions of myocardial ischemia have been simulated to determine disease progression, by way of experimental results and such results shall not be construed as limiting the scope of the present disclosure.

Referring now to the drawings, and more particularly to FIG. 1 through FIG. 7C, where similar reference characters denote corresponding features consistently throughout the figures, there are shown preferred embodiments and these embodiments are described in the context of the following exemplary system and/or method.

FIG. 1 illustrates an exemplary block diagram of a system for determining myocardial ischemia severity based on hemodynamic parameters estimation, in accordance with some embodiments of the present disclosure.

In an embodiment, the system 100 includes processor (s) 104, communication interface (s), alternatively referred as or input/output (I/O) interface(s) 106, and one or more data storage devices or memory 102 operatively coupled to the processor (s) 104. The system 100, with the processor(s) is configured to execute functions of one or more functional blocks of the system 100.

Referring to the components of the system 100, in an embodiment, the processor (s) 104 can be one or more hardware processors 104. In an embodiment, the one or more hardware processors 104 can be implemented as one or more microprocessors, microcomputers, microcontrollers, digital signal processors, central processing units, state machines, logic circuitries, and/or any devices that manipulate signals based on operational instructions. Among other capabilities, the processor(s) 104 is configured to fetch and execute computer-readable instructions stored in the memory. In an embodiment, the system 100 can be implemented in a variety of computing systems, such as laptop computers, notebooks, 10 hand-held devices, workstations, mainframe computers, servers, a network cloud, and the like.

The I/O interface(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface (s) 106 can include one or more ports for connecting a number of devices (nodes) of the system 100 to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 102 comprises a plurality of modules 108 such as the cardiac source module 110 and the hemodynamic module 112 and so on, to implement the functions determine the myocardial ischemic severity using the system 100.

The modules 108 can be an Integrated Circuit (IC) (not shown), external to the memory 102, implemented using a Field-Programmable Gate Array (FPGA) or an Application-Specific Integrated Circuit (ASIC). The names (or expressions or terms) of the modules of functional block within the modules 108 referred herein, are used for explanation and are not construed to be limitation(s). The modules 108 includes the cardiac source module 110 for processing a plurality of Electrophysiology (EP) signals received from a heart surface model as an input, and the hemodynamic module 112 for estimating a plurality of hemodynamic parameters based on processing the plurality of Electrophysiology (EP) signals received from the cardiac source module 110. The cardiac source module 110 and the hemodynamic module 112 are coupled through a contractility function which in turn determines the compliance function of auricles and ventricles which brings pumping function of the heart source model.

Figure 2:
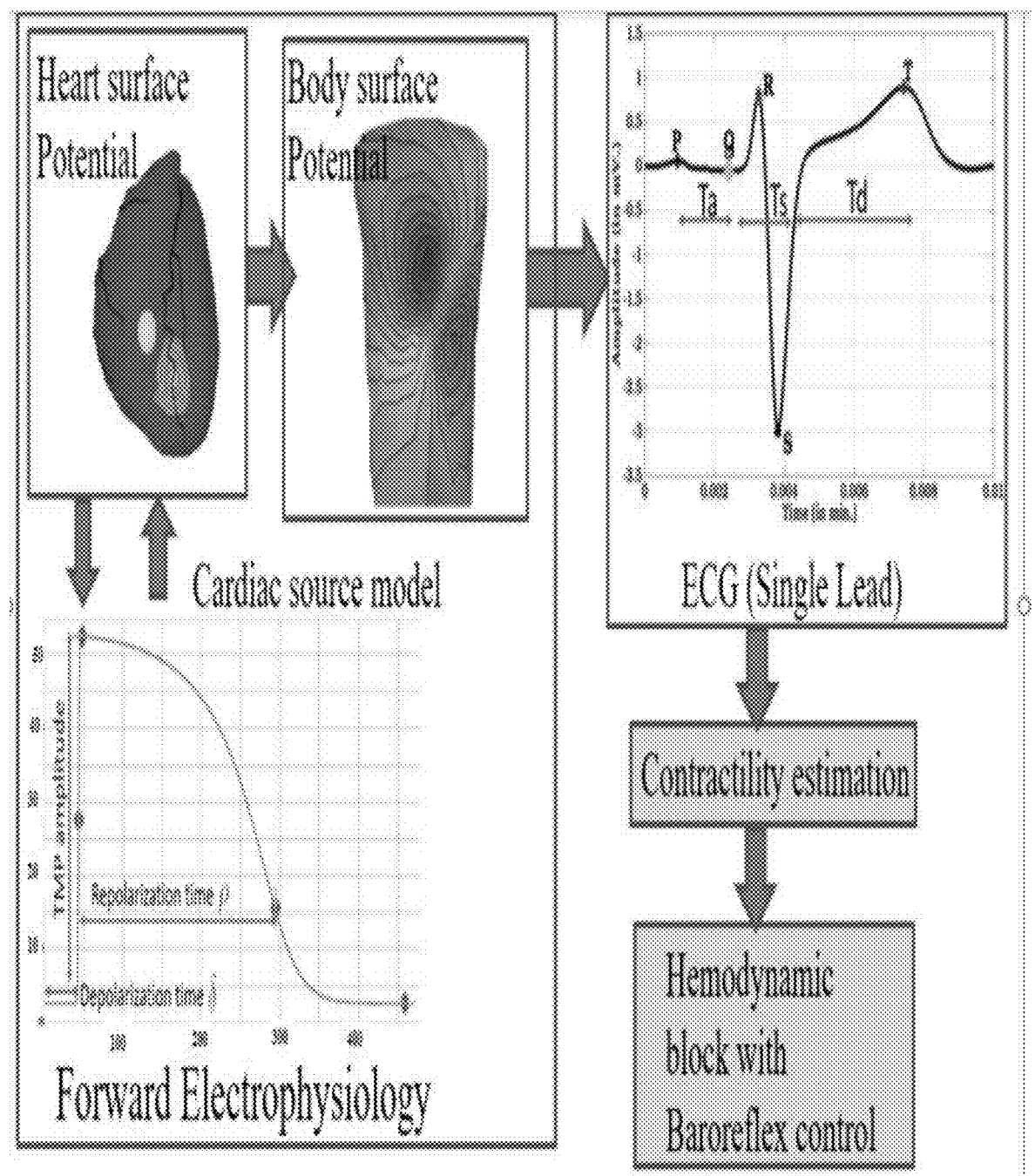
FIG. 2 illustrates an example schematic diagram for determining severity of myocardial ischemia based on hemodynamic parameters estimation using the system of FIG. 1, in accordance with some embodiments of the present disclosure.

FIG. 2 illustrates an example schematic diagram for determining severity of myocardial ischemia based on hemodynamic parameters estimation using the system of FIG. 1, in accordance with some embodiments of the present disclosure. FIG. 2 includes the cardiac source module 110 and the hemodynamic module 112. The cardiac source module 110 comprises a heart surface potential and a body surface potential. The heart surface potential uses myocyte model defining cardiac action potential or a mathematical equivalent approximating the cardiac transmembrane potential (TMP). The body surface potential is calculated by feeding the cardiac transmembrane potential (TMP) through a cardiac propagation model such as monodomain or bidomain equations and boundary conditions through proper torso coupling. These extensive field equations are solved using numerical techniques such as a Finite element method (FEM) for volume integration or a Boundary element method (BEM) for surface integration. Further, the body surface potential is generated for different myocardial ischemia episodes and a single lead ECG template derived to determine the myocardial ischemia progression based on changes in the single lead ECG template morphology, typically during a ventricular repolarization (ST) segment which characterizes ventricular depolarization (QRS) segment of the single lead ECG template.

In one embodiment, the hemodynamic module 112 estimates the output received from the cardiac source model 110 for determining the myocardial ischemic severity. The hemodynamic module 112 consists of a simulation model of patient's heart or heart source model comprising four chambers with a systemic circulation, and a pulmonic circulation along with baroreflex auto regulation and the like. The heart chambers have been modeled as compliant vessels. Further, the pumping of the heart surface model is triggered through an autonomous contractility function derived from the cardiac source module 110. The simulated body surface potential (BSP) of the cardiac source module 110 drives the hemodynamic module 112, which modeled as four chambered heart with the pulmonic circulation and the systemic circulation. The integrated multi-model considers cellular to organ level manifestation of myocardial ischemia to simulate healthy heart dynamics and varying conditions of myocardial ischemia. The ground truth data of a healthy cardiac is generated based on all the varying conditions of ECG, blood pressure, left ventricle dynamics, ejection fraction and Photoplethysmogram (PPG) signal based on medical observations for close match. An example implementation of the system 100 for determining myocardial ischemic severity based on hemodynamic parameter estimation is described further with reference to FIG. 3.

Figure 3:
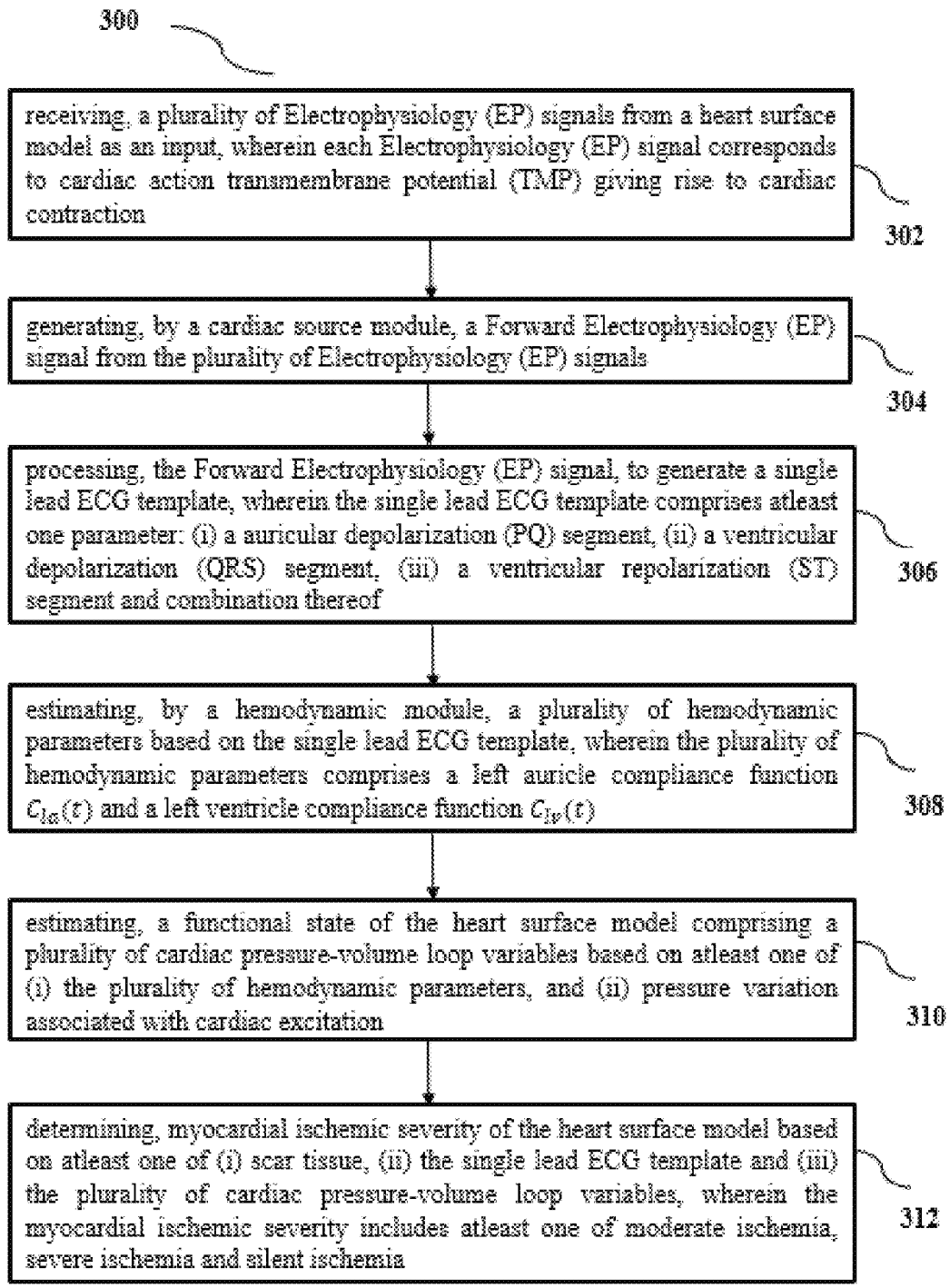
FIG. 3 illustrates a flow diagram for determining myocardial ischemia severity based on hemodynamic parameters estimation using the system of FIG. 1, in accordance with some embodiments of the present disclosure.

FIG. 3 illustrates a flow diagram for determining myocardial ischemia severity based on hemodynamic parameters estimation using the system of FIG. 1, in accordance with some embodiments of the present disclosure.

In an embodiment, the system 100 comprises one or more data storage devices or the memory 102 operatively coupled to the processor(s) 104 and is configured to store instructions for execution of steps of the method 300 by the processor(s) or one or more hardware processors 104. The steps of the method 300 of the present disclosure will now be explained with reference to the components or blocks of the system 100 as depicted in FIG. 1 and FIG. 2 and the steps of flow diagram as depicted in FIG. 3. Although process steps, method steps, techniques or the like may be described in a sequential order, such processes, methods and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

Referring now to the steps of the method 300, at step 302, the one or more hardware processors 104 receive a plurality of Electrophysiology (EP) signals from a heart surface model as an input. Each Electrophysiology (EP) signal from the plurality of Electrophysiology (EP) signals corresponds to cardiac action transmembrane potential (TMP) giving rise to cardiac contraction. The system 100 can be used, for example an anatomical model of patient's heart referred as simulated heart surface model for determining the myocardial ischemic severity. The system 100 receives the plurality of Electrophysiology (EP) signals from a plurality of points of the heart surface model with its associated location information to create a diagnostic map of the heart surface model of the cardiac source module 110.

Referring now to the steps of the method 300, at step 304, the one or more hardware processors 104 generate, via the cardiac source module 110, a Forward Electrophysiology signal from the plurality of Electrophysiology (EP) signal. The plurality of Electrophysiology (EP) signals received from the heart surface model as an input to generate the Forward Electrophysiology signal, referring now to FIG. 2. Electrocardiogram is based on a biophysical model that connects cardiac transmembrane potential (TMP) of representative myocytes on the heart surface model to electrocardiogram (ECG) signal on the surface of body. Geometrical parameters related to atria, ventricle and torso are reconstructed from magnetic resonance imaging.

Referring now to the steps of the method 300, at step 306, the one or more hardware processors 104 process the Forward Electrophysiology signal, to generate a single lead ECG template, wherein the single lead ECG template comprises at least one parameter comprising: (i) a auricular depolarization (PQ) segment, (ii) a ventricular depolarization (QRS) segment, (iii) a ventricular repolarization (ST) segment and combination thereof. Considering the above example, to generate the single lead ECG template, the cardiac source module 110 is expressed as equivalent double layer (EDL) of sources on the closed surface of the atrium and the ventricles. Referring now to FIG. 2, it is analogous to an equivalent source of the currents generated at the cell membrane during depolarization of the myocyte as referred earlier in the cardiac transmembrane potential (TMP). Here, the simulated patients heart surface is divided into a triangular mesh of 1500 elements or nodes, where each node poses an equivalent source which is proportional to the cardiac transmembrane potential (TMP) of the nearest myocyte. Further, time course of strength of the equivalent double layer (EDL) is an analytical function represented as sigmoid curve expressed as product of logistics function involving markers for the timing of the ventricular depolarization (QRS) segment and the ventricular repolarization (ST) segment for approximating the cardiac transmembrane potential (TMP). The source matrix (S) at node 'n' at time instant 't' is as defined below in equation (1), $$S(t;\delta,\rho)=D(t;\delta)R(t;\rho) \quad \text{equation (1)}$$

where, 'D' is the depolarization phase and 'R' is the repolarization phase. The timing of local depolarization at node 'n' is denoted as 'δ'. The interval $\alpha=\rho-\delta$ is taken as a measure of the local action potential duration. Such timing parameters and cardiac transmembrane potential (TMP) amplitudes can be varied to induce different conditions.

In one embodiment, based on the equivalent double layer (EDL), source model local strength at position on 'x' the surface of the myocardium can be mapped to potential generated at location on the body surface as described below in equation (2), $$\phi(t,y)=\int B(y,x)V_m(t,x)d_w(y,x) \quad \text{equation (2)}$$

where, B(y, x) is the transfer function expressing the volume conductor model, considering geometry and conductivity in the chest cavity, $V_m$, is the local transmembrane potential (TMP) at heart surface model, $d_w(y, x)$, is the solid angle subtended at y by the surface element $dS(x)$ of the myocardinal node $S_y$. The volume conductor model as expressed above in equation 2, cannot be solved analytically due to complex asymmetrical shape of individual compartments using the specialized Boundary element method (BEM). Further, potential at discretized body surface model consisting of 'l' lead position can be described as shown below in equation (3), $$\phi(t,l) = \Sigma_n B(l,n) S(t; \delta, \rho) \qquad \text{equation (3)}$$

where, 'B' is a transfer matrix, incorporating the solid angles subtended by source elements as viewed from the nodes of the triangulate surface. The elements of the transfer matrix 'B' expresses the source strengths of all 'n' (n=1500) nodes on the heart surface potentials at 'l' (l=256) lead positions on the torso surface. Further, the resulting matrix 'φ' generates the standard 12 lead ECG template. The generated single lead ECG template serves as the driving signal to the hemodynamic module 112 as described in the next step of the present disclosure.

Figure 4:
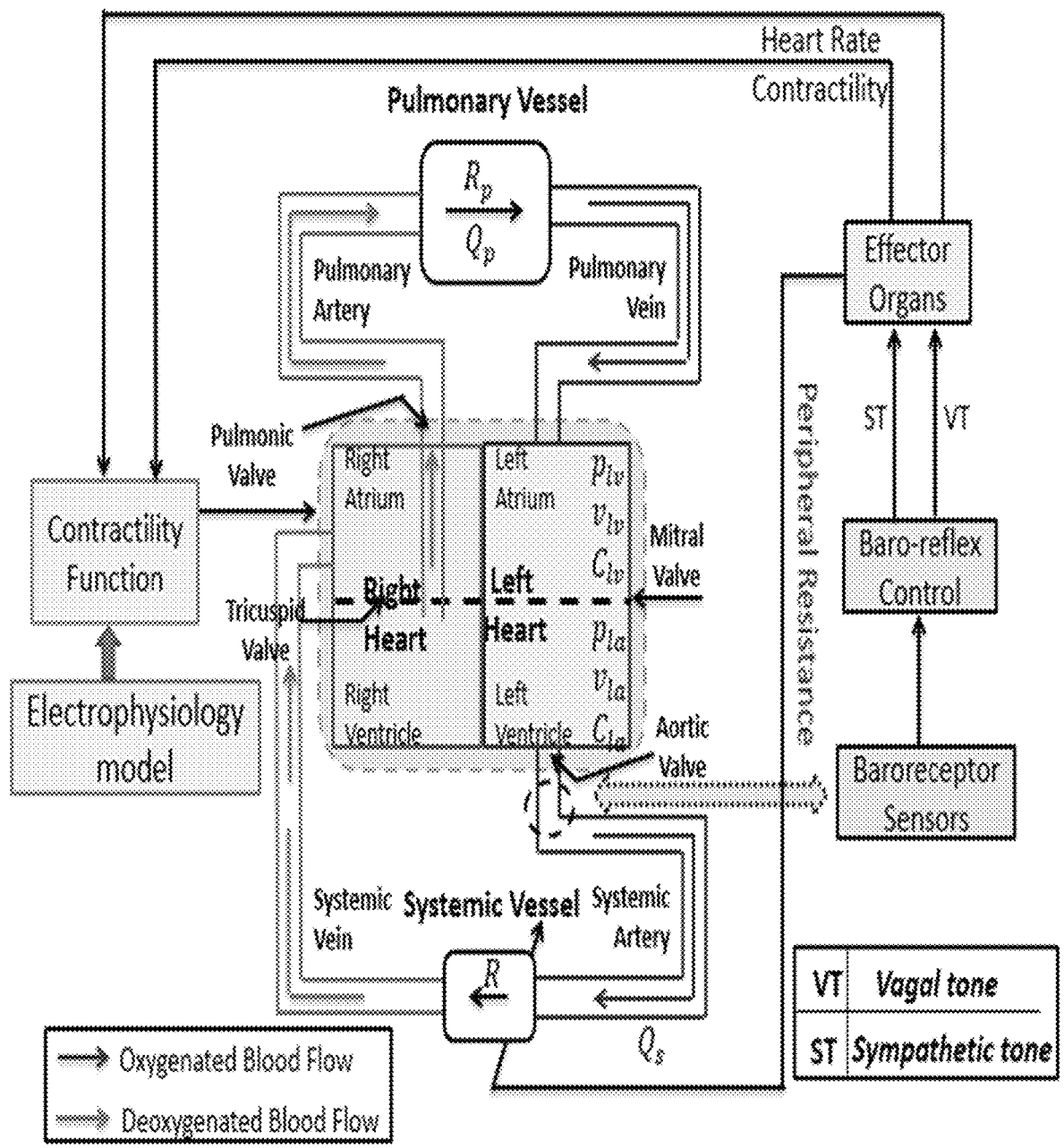
FIG. 4 illustrates schematic representation of a hemodynamic module for estimating hemodynamic parameters using the system of FIG. 1, in accordance with some embodiments of the present disclosure.

Referring now to the steps of the method 300, at step 308, the one or more hardware processors 104 estimate, via the hemodynamic module 112, a plurality of hemodynamic parameters based on the single lead ECG template, wherein the plurality of hemodynamic parameters comprises a left heart atrium compliance function $C_{la}(t)$ and a left heart ventricle compliance function $C_{lv}(t)$. Referring now to FIG. 4, the generated single lead ECG signal served as the driving signal to the hemodynamic module 112 for estimating the left heart atrium compliance function $C_{la}(t)$ and the left heart ventricle compliance function $C_{lv}(t)$. The hemodynamic module 112 consists of simulated heart surface model which includes four chambers with the systemic circulation and the pulmonic circulation along the baroflex auto regulation and the like. The vasculature of major vessels is modeled as combination of resistive and capacitive tube. Further, all the major heart valves have been modeled to work in synchronized manner corresponding to auricular depolarization and ventricular repolarization of the heart chambers, thereby bringing the pulsatile effect with pressure gradient generation and volumetric change in the blood flow. The coupling of cardiac source module 110 and the hemodynamic module 112 enables to determine the compliance of the atrium and the ventricles for the pumping action of the heart surface model. Further, the driving signal lead ECG template received from the cardiac source module 110 is decomposed into its characteristic constituents such as the auricular depolarization (PQ) segment, the ventricular depolarization (QRS) segment and the ventricular repolarization (ST) segment. Changes encoded to modulate compliance function and timing information to control synchronized operation of the four heart chambers.

In one embodiment, the left heart atrium compliance function $C_{la}(t)$ is computed based on at least one of (i) a minimum value of the left heart atrium, (ii) a maximum value of the left heart atrium, (iii) a left heart atrium activation function, and (iv) a time delay in firing between the left heart atrium and the left heart ventricle as described below in equation (4), $$C_{la}(t) = C_{min,la} + 0.5(C_{max,la} - C_{max,la}) A_{la}(t-D) \qquad \text{equation (4)}$$

where, $C_{min,la}$ is the minimum compliance function of the left heart atrium, $C_{max,la}$ is the maximum compliance function of the left heart atrium, D is the time delay in firing between the left heart atrium and the left heart ventricle, and $A_{la}$ is the left heart atrium activation function. Further, the left heart atrium activation function is computed based on the left heart atrium activation time analogous to the auricular depolarization (PQ) segment and the time duration of the cardiac cycle as described below in equation (5), $$A_{la} = \begin{cases} 0 & 0 \leq t \leq T_a \\ 1 - \cos\left(2\pi \dfrac{t - T_a}{T - T_a}\right) & T_a \leq t < T \end{cases} \qquad \text{equation (5)}$$

where, $T_a$, is the left heart atrium activation time which is analogous to the (PQ) segment, and T, is the time duration of the cardiac cycle.

In one embodiment, the left heart ventricle compliance function $C_{lv}(t)$ is computed based on the end systolic compliance and the left heart ventricle activation function. The product of end systolic compliance and the left heart ventricle activation function as described below in equation (6), $$C_{lv}(t) = C_{es,lv} * A_{lv}(t) \qquad \text{equation (6)}$$

where, $C_{es,lv}$ is the end systolic compliance, and $A_{lv}(t)$ is the activation function for the left heart ventricle.

Further, the left heart ventricle activation function is computed based on systolic and diastolic time duration of the cardiac cycle analogous to (i) the ventricular depolarization (QRS) segment, and (ii) the ventricular repolarization (ST) segment as described below in equation (7), $$A_{lv} = \begin{cases} \dfrac{1 - \cos\left(\left(\dfrac{t}{T_s}\right)\pi\right)}{2} & 0 \leq t \leq T_s \\ \dfrac{1 - \cos((t - T_s)/(T_D - T_s)\pi)}{2} & T_s \leq t < T_d \\ 0 & T_d \leq t < T \end{cases} \qquad \text{equation (7)}$$

where, $T_s$ and $T_d$ are the systolic and diastolic time duration of the cardiac cycle analogous to the ventricular depolarization (QRS) segment and the ventricular repolarization (ST) segment associated with the single lead ECG template.

Referring now to the steps of the method 300, at step 310, the one or more hardware processors 104 estimate a plurality of cardiac pressure-volume loop variables based on at least one of (i) the plurality of hemodynamic parameters, and (ii) pressure variation associated with cardiac excitation. The plurality of cardiac pressure-volume loop variables includes at least one of (i) a dynamic change observed in a systemic artery pressure, (ii) a dynamic change observed in a left heart ventricle pressure and (iii) a dynamic change observed in a right ventricle pressure.

The dynamic change observed in the systemic artery pressure ($\dot{P}_{sa}$) is estimated based on at least one of (i) a systemic artery compliance, (ii) the left heart ventricle pressure, (iii) a systemic ventricle pressure, (iv) a systemic artery pressure, (v) a resistance value observed in systemic vessels, and (vi) a resistance value observed in aortic vessel which is described below in equation (8), $$\dot{P}_{sa} = \dfrac{1}{C_{sa}}\left[\dfrac{p_{lv} - p_{sa}}{R_{Ao}} - \dfrac{p_{sa} - p_{sv}}{R}\right] \qquad \text{equation (8)}$$

where, $\dot{P}_{sa}$ is the pressure variation observed in systemic artery expressed as the dynamic change in the systemic artery compliance function, pressure gradients, valves and vessel resistance, $C_{sa}$ is the systemic artery compliance, $p_{lv}$, is the left heart ventricle pressure, $p_{sa}$ is the systemic artery pressure, $R_{Ao}$ is the resistance value observed in aortic vessel, and R is the resistance value observed in systemic vessels.

The dynamic change observed in the left heart ventricle pressure ($\dot{P}_{lv}$)) is estimated based on at least one of (i) the left heart ventricle compliance function, (ii) the left heart ventricle pressure, (iii) a pulmonary vein pressure, (iv) the systemic artery pressure, (v) a resistance value observed in mitral vessel, and (vi) the resistance value observed in aortic vessel which is described below in equation (9), $$\dot{P}_{lv} = \frac{C_{lv}'(t)}{C_{lv}(t)} p_{lv} + \frac{1}{C_{lv}(t)} \left[ \frac{p_{pv} - p_{lv}}{R_{Mi}} - \frac{p_{lv} - p_{sa}}{R_{Ao}} \right] \quad \text{equation (9)}$$

$\dot{P}_{lv}$ is the pressure variation observed in left ventricle expressed as the dynamic change in the left ventricle compliance function, pressure gradients, valves and vessel resistance, $C_{lv}(t)$ is the left heart ventricle compliance function, $p_{lv}$ is the left heart ventricle pressure, $p_{pv}$, is the pulmonary vein pressure $p_{sa}$ is the systemic artery pressure, $R_{Mi}$ is the resistance value observed in mitral vessel, and $R_{Ao}$, is the resistance value observed in aortic vessel.

The dynamic change observed in the right heart ventricle pressure ($\dot{P}_{rv}$) is estimated based on at least one of (i) the right heart ventricle compliance function, (ii) a systemic vein pressure (iii) the right heart ventricle pressure, (iv) a resistance value observed in tricuspid vessel, (v) a pulmonary artery pressure, and (vi) a resistance value observed in pulmonary valve which is described below in equation (10), $$\dot{P}_{rv} = \frac{C_{rv}'(t)}{C_{rv}(t)} p_{rv} + \frac{1}{C_{rv}(t)} \left[ \frac{p_{sv} - p_{rv}}{R_{Tr}} - \frac{p_{pr} - p_{pa}}{R_{Pv}} \right] \quad \text{equation (10)}$$

where, $\dot{P}_{rv}$ is the pressure variation in right ventricle during the cardiac cycle expressed as the dynamic changes in the right ventricle compliance, pressure gradient, systemic vein pressure, pulmonary artery pressure and vessel resistance, $C_{rv}(t)$ is the right ventricle compliance function, $p_{rv}$ is the right heart ventricle pressure, $p_{rv}$ is the systemic vein pressure, $p_{pa}$ is the pulmonary artery pressure, $R_{Tr}$ is the resistance value observed in tricuspid vessel, and $R_{Pu}$, is the resistance value observed in pulmonary valve. Further, the hemodynamic module 112 determines the plurality of hemodynamic parameters such as the arterial blood pressure, the left heart ventricle, the end systolic and diastolic volume (ESV, EDV), the ejection fraction (EF), the cardiac output (CO), the stroke volume (SV) and the end systolic and end diastolic pressure volume ratio (ESPVR, EDPVR) can be calculated which reveals concise information related to the state of heart and cardiovascular system.

Referring now to the steps of the method 300, at step 312, the one or more hardware processors 104 determine myocardial ischemic severity of the heart surface model based on at least one of (i) a scar tissue size, (ii) a velocity reduction value of cardiac affected region, (iii) the transmembrane potential (TMP) amplitude and repolarization time, (iv) the single lead ECG template and, (v) the plurality of cardiac pressure-volume loop variables. The myocardial ischemic severity includes one of moderate ischemia, severe ischemia and silent ischemia. In another embodiment, the simulated myocardial ischemia as an occlusion in the left anterior descending artery (LAD), effecting apical anterior and anterio-septal area of the heart surface model. Cellular etiology of the myocardial ischemia suggests variational effects in ionic concentration at cell level which manifests itself in the form of action potential or cardiac transmembrane potential (TMP) on the cardiac surface model 110. Specifically, the pathophysiology of ischemic effect can be simulated by inducing the following conditions:

(i) Reduction of cardiac transmembrane potential (TMP) amplitude corresponding to the reduction in strength of effected area of myocardial ischemia.

(ii) Reduction in repolarization time, linked to imbalance in Ca++ pump due to excessive extracellular K+ion.

(iii) Decrease in propagation velocity in the affected tissue due to scar formation.

Further, these changes were incorporated in the cardiac source module 110, by changing specific parameters of the cardiac transmembrane potential (TMP), such as changing the repolarization time, maximum amplitude, depolarization time and thereof in and around the area of the left anterior descending artery (LAD). Further, the affected determined ischemic regions were modeled as 'scar tissues', dimension of these scar tissue were varied based on disease progression.

Moderate myocardial ischemia severity is determined based on the scar tissue size, the velocity reduction value of cardiac affected region and the cardiac transmembrane potential (TMP) amplitude and repolarization time. The scar tissue size for moderate myocardial ischemia varies between a first threshold value and a second threshold value, wherein the first threshold value serving as a minimum value of 25 mm and the second threshold value serving as a maximum value of about 35 mm. The velocity reduction value of cardiac affected region is equal to a predetermined value, wherein this velocity value of about 50%. The cardiac transmembrane potential (TMP) amplitude and repolarization time ranges between a first repolarization time value and a second repolarization time value, wherein the first repolarization time value serving as a minimum value of about 18% and the second repolarization time value serving as a maximum value of about 24%. The method determines the cardiac source module 110 belongs to the moderate myocardial ischemia based on the specified conditions.

Severe myocardial ischemia severity is determined based on the scar tissue size, the velocity reduction value of cardiac affected region and the cardiac transmembrane potential (TMP) amplitude and repolarization time. The scar tissue size for severe myocardial ischemia varies between a first predetermined value and a second predetermined value, wherein the first predetermined value is 40 mm and the second predetermined value is 55 mm. The velocity reduction value of cardiac affected region is equal to a velocity value, wherein this velocity value is of about 50%. The cardiac transmembrane potential (TMP) amplitude and repolarization time ranges between a between a first transmembrane potential amplitude value and a second transmembrane potential amplitude value, wherein the first transmembrane potential amplitude value is minimum value of 30% and the second transmembrane potential amplitude value is maximum value of about 38%. The method determines the cardiac source module 110 belongs to the moderate myocardial ischemia based on the specified conditions Silent myocardial ischemia severity is determined based on the scar tissue size, the velocity reduction value of cardiac affected region and the cardiac transmembrane potential (TMP) amplitude and repolarization time. The scar tissue size for silent myocardial ischemia varies between a first predefined value and a second predefined value, wherein the first predefined value is 12 mm and the second predefined value is 16 mm. The velocity reduction value of cardiac affected region is equal to a velocity value, wherein the velocity value is of about 50%. The cardiac transmembrane potential (TMP) amplitude and repolarization time ranges between a first transmembrane potential value and a second transmembrane potential value, wherein the first transmembrane potential value is minimum of about 12% and the second transmembrane potential value is a maximum value of about 17%. The method determines the cardiac source module 110 belongs to the moderate myocardial ischemia based on the specified conditions. Further, the silent myocardial ischemia where pathological manifestation happens only during stress or exercise conditions.

Figure 5:
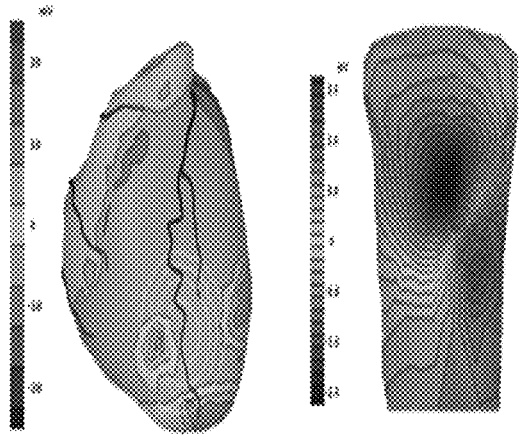
FIG. 5 illustrates ventricular systole and diastole myocardial conditions of healthy conditions and ischemic conditions, in accordance with some embodiments of the present disclosure.
Figure 5:
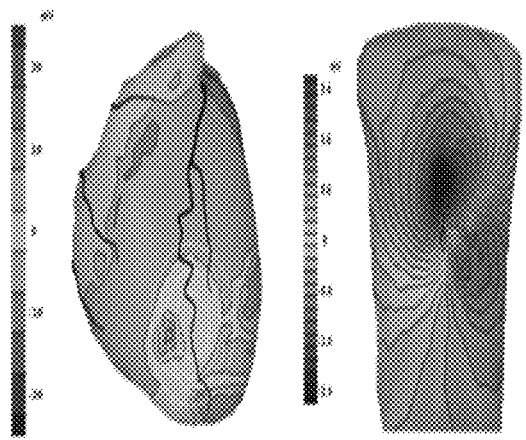
Figure 5:
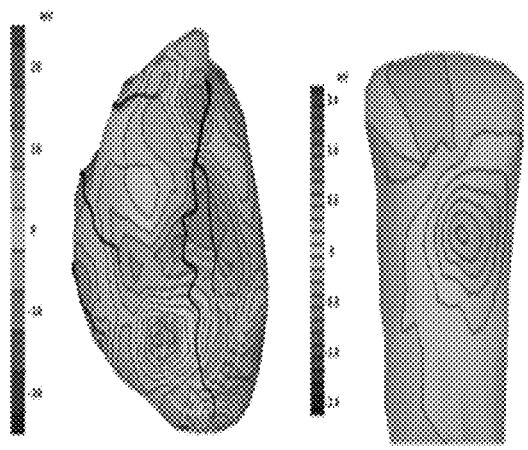
Figure 5:
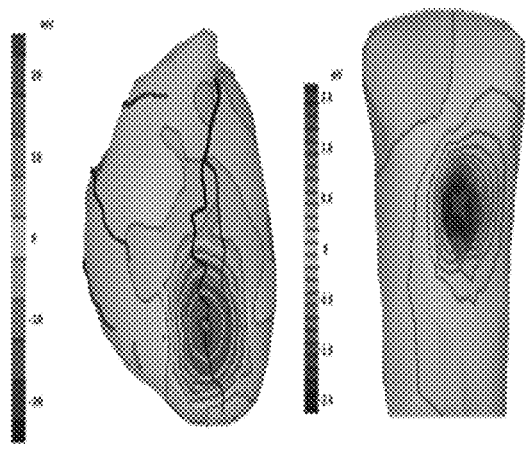

FIG. 5 illustrates ventricular systole and diastole myocardial conditions of healthy conditions and ischemic conditions, in accordance with some embodiments of the present disclosure. More specifically, FIG. 5 depicts myocardial ischemia conditions of healthy cardiac and ischemic affected myocardium. Two separate instances represent the ventricular depolarization (QRS) segment at 220 ms during the time of QRS complex generation and the ventricular repolarization (ST) segment at 440 ms associated with the ECG template.

Figure 6A:
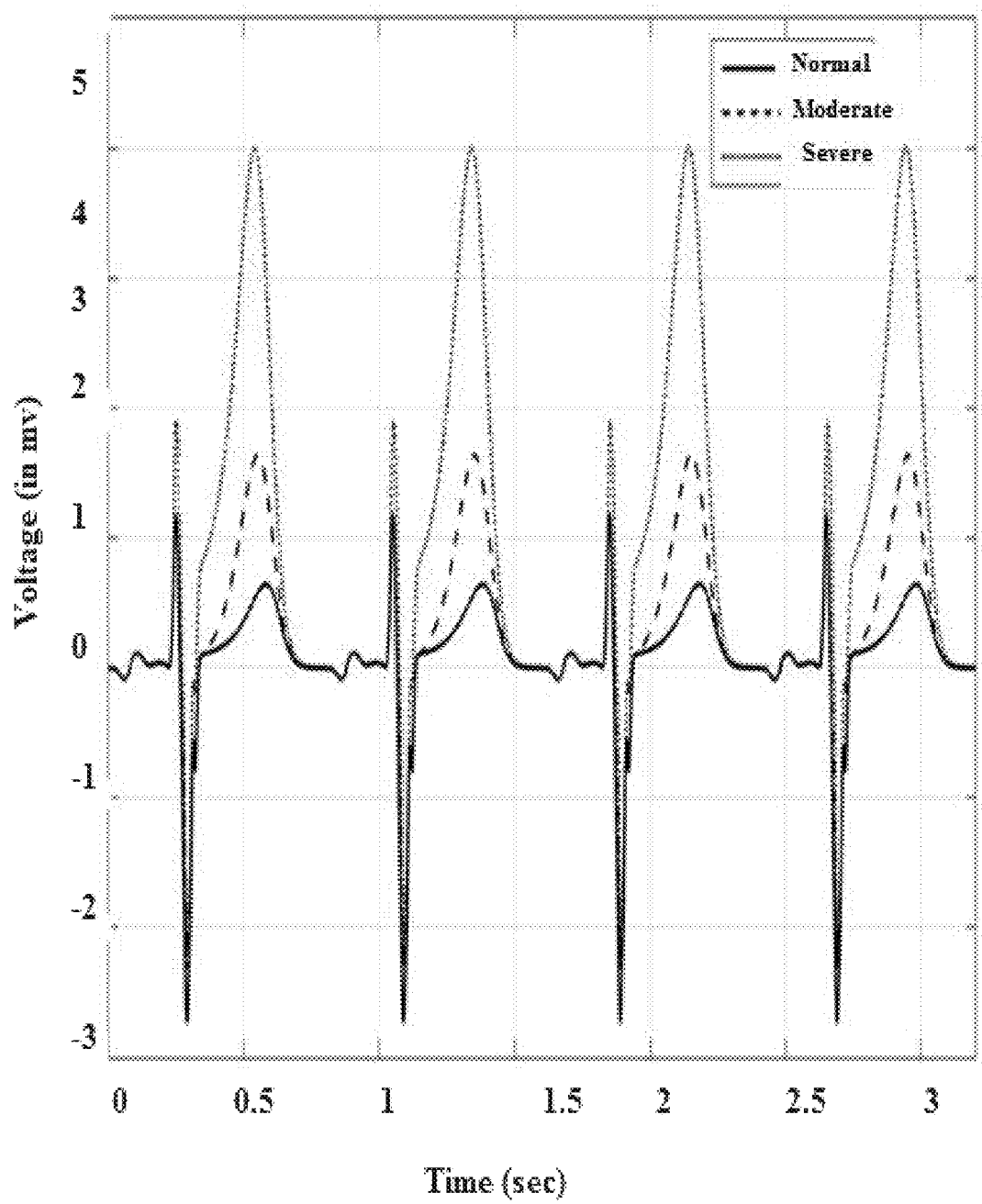
FIG. 6A illustrates simulated ECG signals showing myocardial ischemic severity, in accordance with some embodiments of the present disclosure.

FIG. 6A illustrates simulated ECG signals showing myocardial ischemic severity, in accordance with some embodiments of the present disclosure. As evident from FIG. 6A, illustrates a simulated single lead ECG template captures large changes in the ventricular repolarization (ST) segment correlates with the ventricular repolarization phase. Further, transmural myocardial ischemia results in the ventricular repolarization (ST) segments often with 'Q' wave inversion. Change in the ventricular repolarization (ST) segment refers to generic weakness in the myocardium around the affected area and the effect magnifies with increase in size of scar tissue.

Figure 6B:
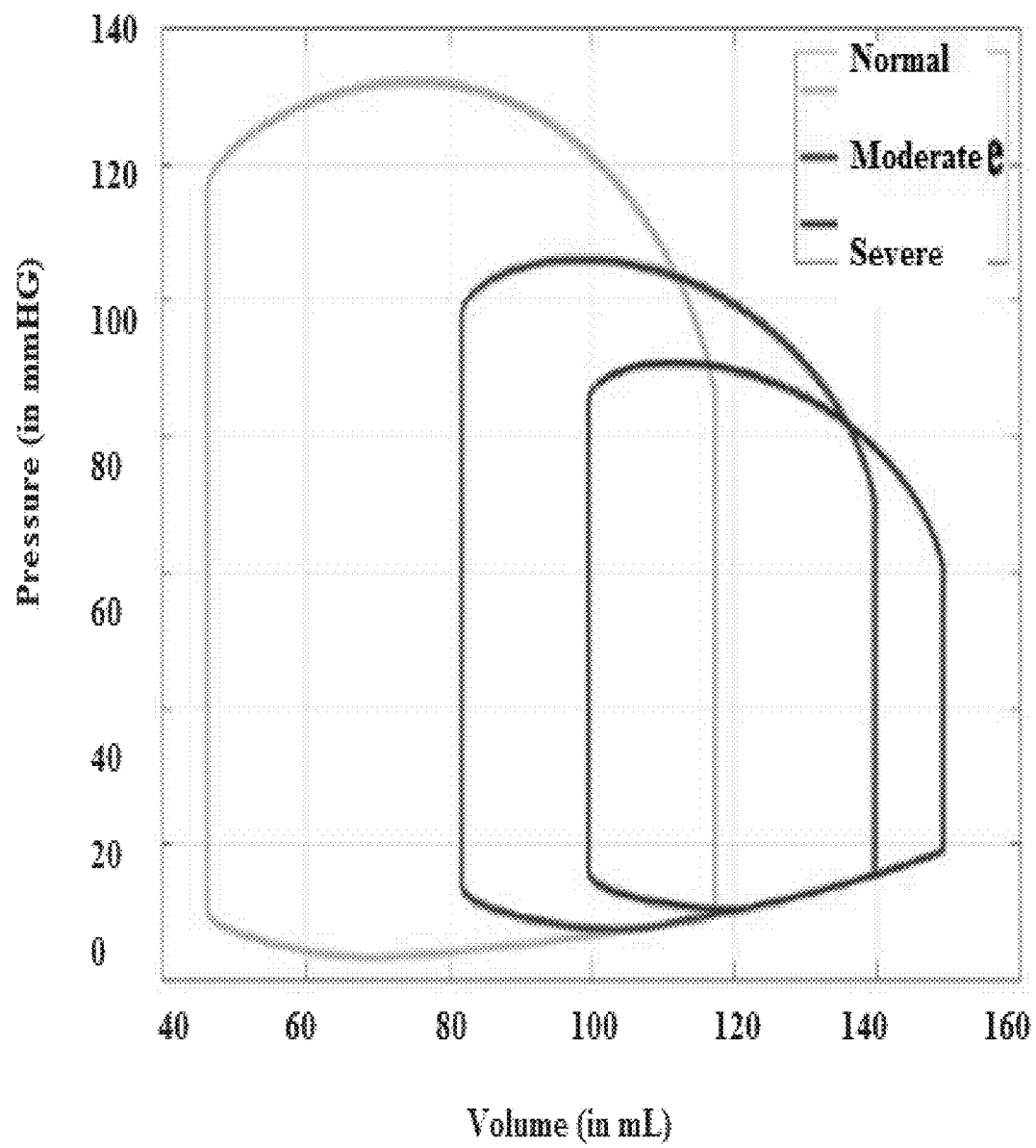
FIG. 6B illustrates pressure volume loop showing left heart ventricle with myocardial ischemic severity in accordance with some embodiments of the present disclosure.

FIG. 6B illustrates pressure volume loop showing left heart ventricle with myocardial ischemic severity in accordance with some embodiments of the present disclosure. The weakness observed in turn effects the pumping function, resulting in the left heart ventricle cardiac pressure-volume loop variables as shown. The cardiac pressure-volume loop variables of the moderate and the severe ischemia in comparison to the healthy pressure volume, shows reduction in cardiac output and ejection fraction and a general trend of systolic dysfunction, commonly related with ischemia.

Figure 6C:
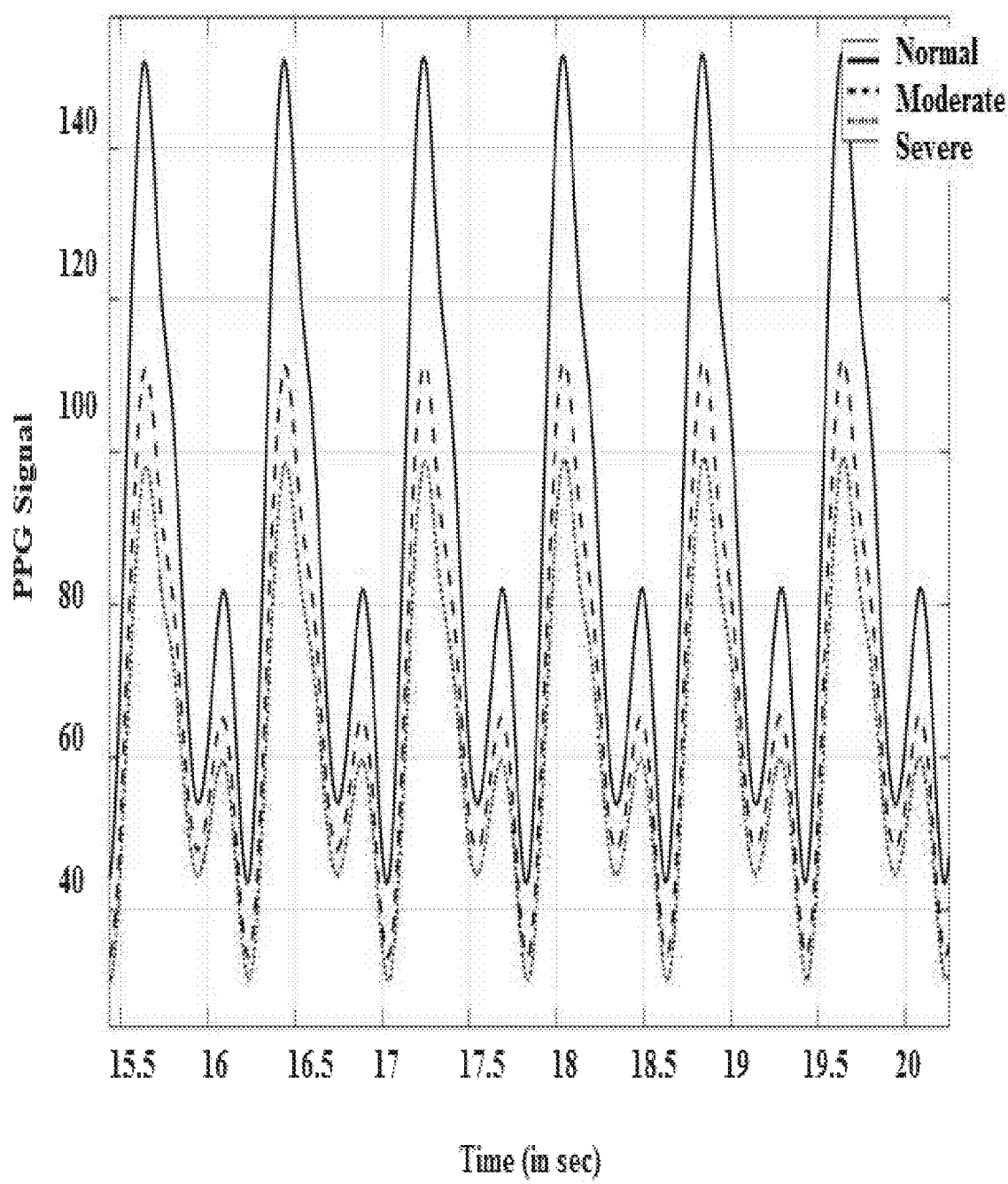
FIG. 6C illustrates simulated PPG signals showing myocardial ischemic severity in accordance with some embodiments of the present disclosure.

FIG. 6C illustrates simulated PPG signals showing myocardial ischemic severity in accordance with some embodiments of the present disclosure. Simulated photoplethysmogram (PPG) signal, shown in figure reveals interesting insights on myocardial ischemia conditions. There is a reduction in photoplethysmogram (PPG) signal amplitude in both the systolic and the diastolic phases, related with the decreasing stroke volume of heart as ischemia progresses. This is particularly because photoplethysmogram (PPG) sensors are noninvasive sensors and are implemented in many smart phones and commercially available wearables. Morphological changes seen in these type of signals and when correlated with ischemic behavior can aid in early screening of myocardial ischemic conditions.

Figure 7A:
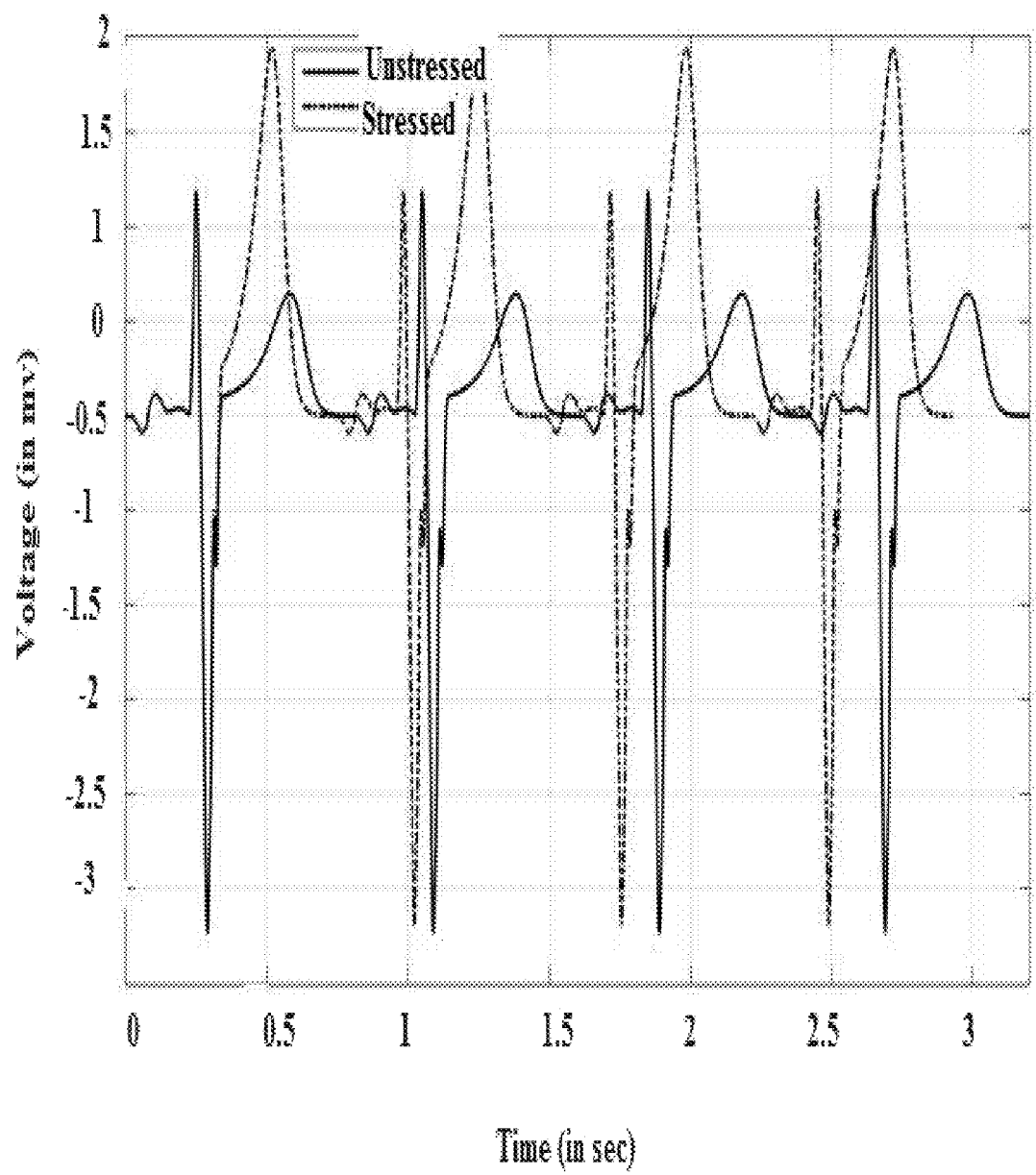
FIG. 7A illustrates simulated ECG signals for silent myocardial ischemia showing stressed and destressed condition in accordance with some embodiments of the present disclosure.

FIG. 7A illustrates simulated ECG signals for silent myocardial ischemia showing stressed and destressed condition in accordance with some embodiments of the present disclosure. Ischemia is generally associated with chest pain and pathological changes in ventricular repolarization (ST) segment of the single lead ECG template which are easy symptoms for diagnosis. However, ischemic episodes are asymptomatic or silent in as many as 80% of cases where there is no associated symptom manifestation observed during daily ambulatory activity but results in maximum cases of sudden cardiac death due to lack of manifestation at diagnosis. Silent ischemia can only be detected under stress testing, where the hidden disease conditions gets reflected in the ECG morphology. In one embodiment, Table 1 provides different simulated conditions with the plurality of hemodynamic parameters. It is evident from the table 1 that as ischemic behavior magnifies the detectable changes in EF, SV, CO, ESPVR correlates with ventricular muscle stiffness and EDPVR correlates with contractility.

TABLE 1

Cardiac Parameters for various hemodynamic parameters

| Conditions | Heart rate (beats/min) | BP (mm of Hg) | ESV (ml) | EDV (ml) | ESPVR | EDPVR | EF | SV (ml) | CO (l/min) |
|---|---|---|---|---|---|---|---|---|---|
| Healthy | 75 | 125/5 | 46.13 | 117.1 | 2.52 | 0.16 | 0.606 | 70.97 | 5.25 |
| Moderate ischemia | 75 | 105/70 | 81.72 | 139.6 | 1.20 | 0.26 | 0.414 | 57.88 | 4.34 |
| Severe ischemia | 75 | 90/60 | 99.49 | 149.3 | 0.86 | 0.36 | 0.33 | 49.81 | 3.73 |
| Silent ischemia (unstressed) | 75 | 125/85 | 46.2 | 117.3 | 2.52 | 0.15 | 0.606 | 71.1 | 5.73 |
| Silent ischemia (stressed) | 92 | 100/65 | 88.37 | 142.6 | 1.07 | 0.29 | 0.38 | 54.23 | 4.96 |

Healthy, moderate, severe and silent ischemic condition (unstressed) are simulated at heart rate of 75 beats/min, during the experiments conducted by the embodiments of the present disclosure. For silent ischemia stressed condition, the single lead ECG template was simulated at heart rate of 92 beats/min, during the experiments conducted by the embodiments of the present disclosure. Blood pressure of the silent myocardial ischemia case under stressed condition revealed a lower diastolic range compared to unstressed, which is another indication of electrical conduction disorder in myocardium.

Figure 7B:
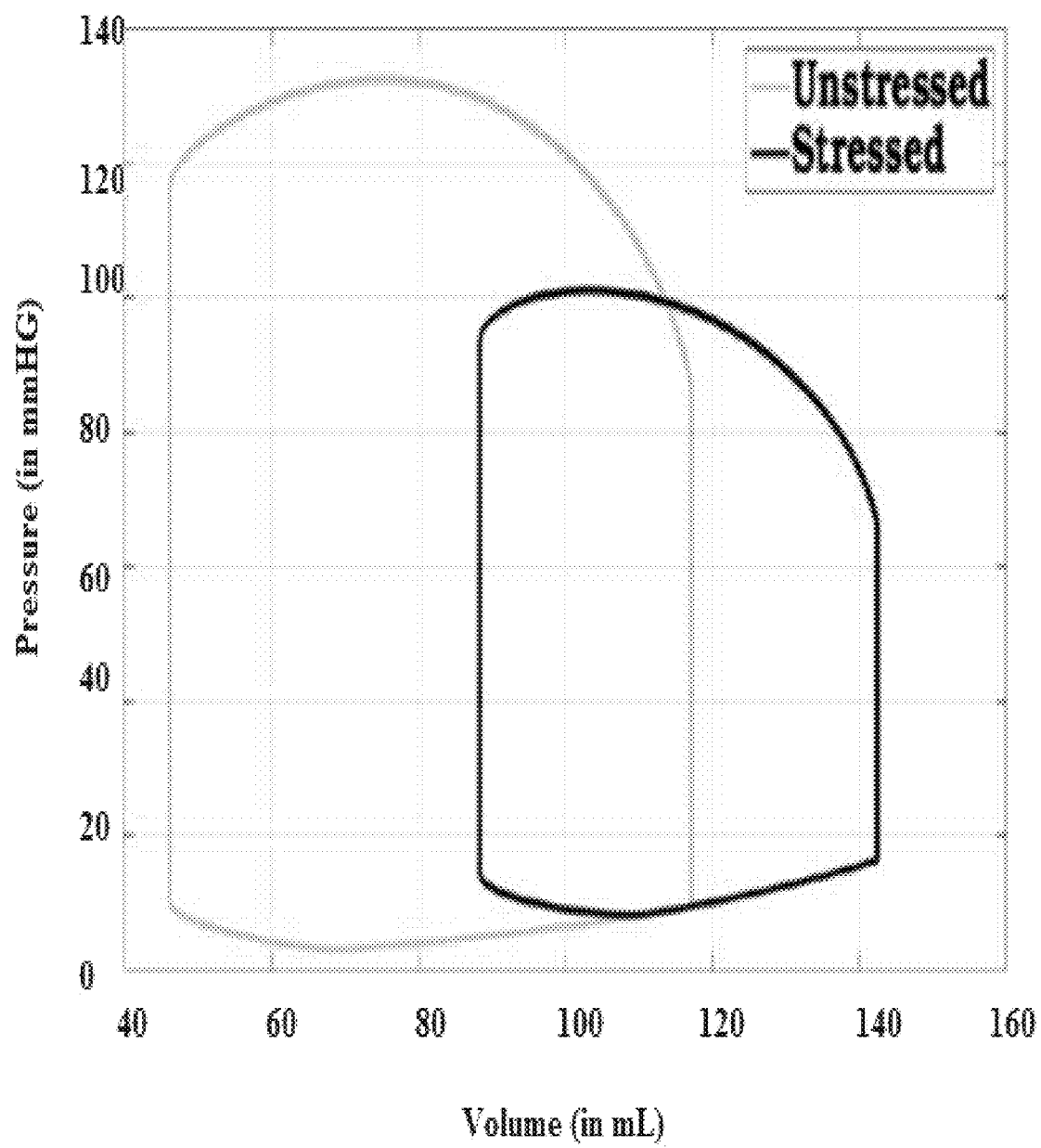
FIG. 7B illustrates pressure volume loop showing left heart ventricle for silent myocardial ischemia showing stressed and destressed condition in accordance with some embodiments of the present disclosure.
Figure 7C:
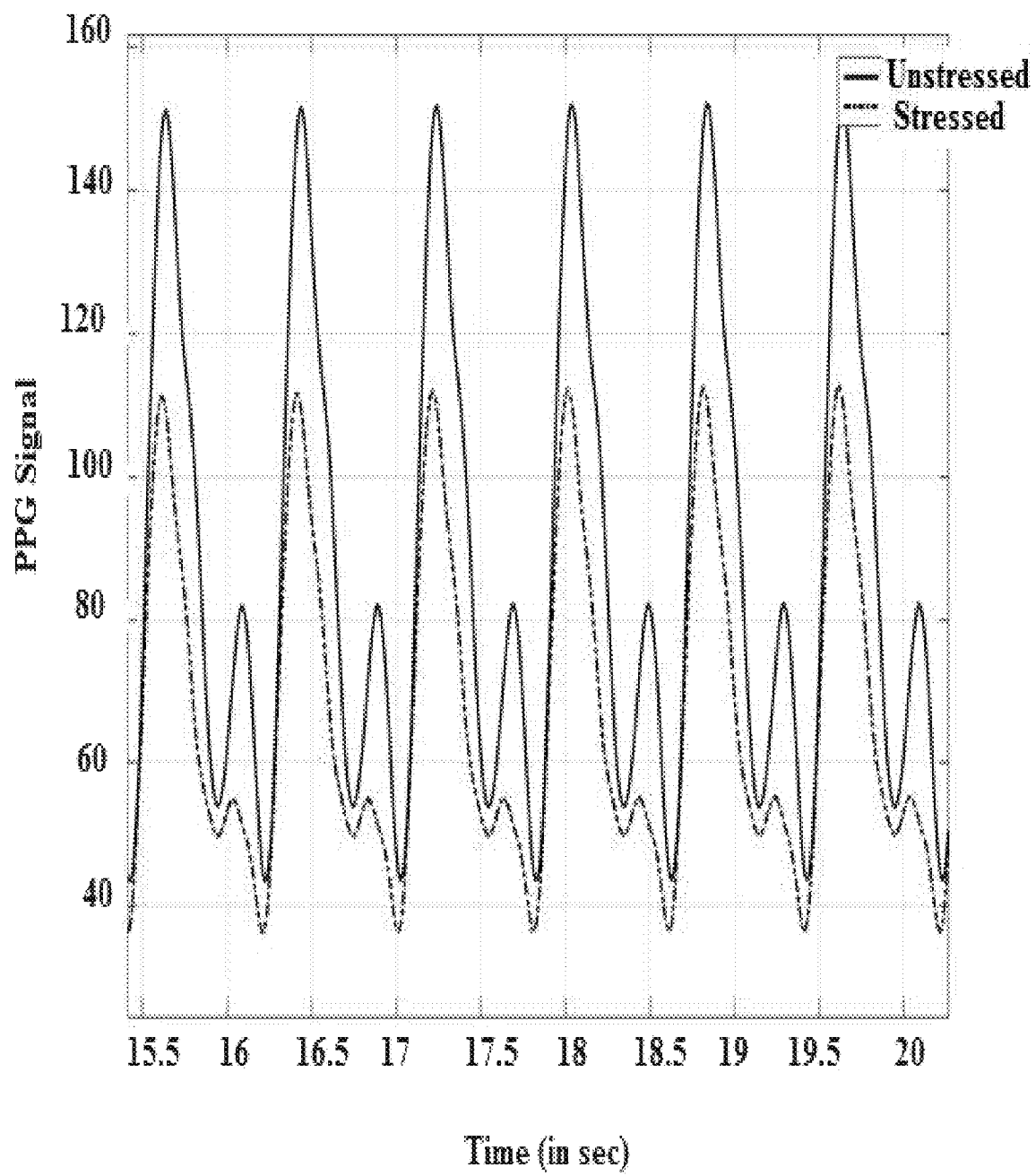
FIG. 7C illustrates simulated PPG signals for silent myocardial ischemia showing stressed and destressed condition in accordance with some embodiments of the present disclosure.

FIG. 7B illustrates pressure volume loop showing left heart ventricle for silent myocardial ischemia showing stressed and destressed condition in accordance with some embodiments of the present disclosure. Stress scenario is simulated with an increased heart rate, as evident during exercise or stress condition. As seen from FIG. 7B, ECG during normal condition is similar to the healthy template, irrespective of small scar area simulation. As the heart rate is increased, ECG morphology changes from normal to pathological. Referring now to FIG. 7C similar observations were made in Pressure-Volume (PV) loop dynamics and PPG generation where unstressed condition replicates normal behavior, whereas under stress, EF decreases significantly.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address unresolved problem of myocardial ischemia severity. The embodiment thus provides determining myocardial ischemia based on hemodynamic parameters estimation. Moreover, the embodiments herein further provide a cardiac model to capture the changes occurred in Electrophysiology (EP) signal from the plurality of Electrophysiology (EP) signals of the heart dynamics during myocardial ischemia. The changes occurred in the cardiac source module 110 serve as driving signal to the hemodynamic module 112 of cardiovascular system. This determines disease progression and its manifestation not only at the electric conduction level but also at the mechanical functioning of heart. Reflection of change in electric parameters over the hemodynamic variables like ejection fraction aids in a holistic understanding of the disease progression and analysis. The present disclosure is an efficient simulation platform that enables study of physiological parameters and deeper understanding of myocardial disease progression. The virtual simulation method serves as digital twin offers to the patient and the care givers/doctors to implement digital therapy/medication to find the best possible prescription. This in turn provides different analysis in stress condition.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for determining myocardial ischemia severity based on hemodynamic parameters estimation, the method comprising:
receiving, via one or more hardware processors, a plurality of Electrophysiology (EP) signals from a heart surface model as an input, wherein each Electrophysiology (EP) signal from the plurality of Electrophysiology (EP) signals corresponds to cardiac transmembrane potential (TMP) giving rise to cardiac contraction, wherein the cardiac transmembrane potential (TMP) of the heart surface model is determined through a contractility function and wherein the contractility function determines a compliance function of auricles and ventricles;

generating, via the one or more hardware processors, by a cardiac source module, a Forward Electrophysiology signal from the plurality of Electrophysiology (EP) signals;

processing, via the one or more hardware processors, the Forward Electrophysiology signal, to generate a single lead ECG template, wherein the single lead ECG template comprises at least one of a characteristic constituent comprising: (i) a auricular depolarization (PQ) segment, (ii) a ventricular depolarization (QRS) segment, (iii) a ventricular repolarization (ST) segment and combination thereof, wherein to generate the single lead ECG template, the cardiac source module is expressed as equivalent double layer of sources on closed surface of atrium and ventricles, wherein the single lead ECG template is generated based on a biophysical model that connects the cardiac transmembrane potential (TMP) of representative myocytes on the heart surface model to an electrocardiogram (ECG) signal on surface of a body, and wherein the generated single lead ECG template serves as a driving signal to a hemodynamic module;

estimating, via the one or more hardware processors, by the hemodynamic module, a plurality of hemodynamic parameters based on the single lead ECG template, wherein the plurality of hemodynamic parameters comprises a left heart atrium compliance function $C_{la}(t)$ and a left heart ventricle compliance function $C_{lv}(t)$, wherein the left heart atrium compliance function $C_{la}(t)$ is computed based on at least one of (i) a minimum value of the left heart atrium, (ii) a maximum value of the left heart atrium, (iii) a left heart atrium activation function $(A_{la})$, and (iv) a time delay in firing between the left heart atrium and the left heart ventricle, wherein the left heart ventricle activation function $(A_{lv}(t))$ is computed based on systolic and diastolic time duration of the cardiac cycle analogous to (i) the ventricular depolarization (QRS) segment, and (ii) the ventricular repolarization (ST) segment and wherein the left heart ventricle compliance function $C_{lv}(t)$ is computed based on an end systolic compliance and the left heart ventricle activation function $(A_{lv}(t))$;

estimating, via the one or more hardware processors, a plurality of cardiac pressure-volume loop variables based on at least one of (i) the plurality of hemodynamic parameters, and (ii) pressure variation associated with cardiac excitation, and wherein the plurality of cardiac pressure-volume loop variables includes at least one of (i) a dynamic change observed in a systemic artery pressure is estimated based on at least one of (i) a systemic artery compliance, (ii) the left heart ventricle pressure, (iii) a systemic ventricle pressure, (iv) a systemic artery pressure, (v) a resistance value observed in systemic vessels, and (vi) a resistance value observed in aortic vessel, (ii) a dynamic change observed in a left heart ventricle pressure is estimated based on at least one of (i) the left heart ventricle compliance function, (ii) the left heart ventricle pressure, (iii) a pulmonary vein pressure, (iv) the systemic artery pressure, (v) a resistance value observed in mitral vessel, and (vi) a resistance value observed in aortic vessel and (iii) a dynamic change observed in a right ventricle pressure is estimated based on at least one of (i) the right heart ventricle compliance function, (ii) a systemic vein pressure, (iii) the right heart ventricle pressure, (iv) a resistance value observed in tricuspid vessel, (v) a pulmonary artery pressure, and (vi) a resistance value observed in pulmonary valve; and determining, via the one or more hardware processors, myocardial ischemia severity of the heart surface model based on (i) a scar tissue size, (ii) a velocity reduction value of the cardiac affected region, (iii) a transmembrane potential (TMP) amplitude and repolarization time, (iv) the single lead ECG template and (v) the plurality of cardiac pressure-volume loop variables, wherein the myocardial ischemia severity includes one of moderate ischemia, severe ischemia and silent ischemia, thereby facilitating in generation of synthetic data for disease classification pertaining to a coronary artery.

2. The method as claimed in claim 1, wherein the left heart atrium activation function $(A_{la})$ is computed based on left heart atrium activation time analogous to the auricular depolarization (PQ) segment and the time duration of the cardiac cycle.

3. The method as claimed in claim 1, wherein the moderate myocardial ischemia is determined if (i) the scar tissue size varies between a first threshold value and a second threshold value, (ii) the velocity reduction value of cardiac affected region is equal to a velocity value, and (iii) the cardiac transmembrane potential (TMP) amplitude and repolarization time range between a first repolarization time value and a second repolarization time value.

4. The method as claimed in claim 1, wherein the severe myocardial ischemia is determined if (i) the scar tissue size varies between a first predetermined value and a second predetermined value, (ii) the velocity reduction value of cardiac affected region is equal to a velocity value, and (iii) the cardiac transmembrane potential (TMP) amplitude and repolarization time range between a first transmembrane potential amplitude value and a second transmembrane potential amplitude value.

5. The method as claimed in claim 1, wherein the silent myocardial ischemia is determined if (i) the scar tissue size varies between a first predefined value and a second predefined value, (ii) the velocity reduction value of cardiac affected region is equal to a velocity value, and (iii) the cardiac transmembrane potential (TMP) amplitude and repolarization time range between a first transmembrane potential value and a second transmembrane potential value.

6. A system, for determining myocardial ischemia severity based on hemodynamic parameters estimation, the system comprises:

a memory storing instructions;

one or more communication interfaces; and one or more hardware processors coupled to the memory via the one or more communication interfaces, wherein the one or more hardware processors are configured by the instructions to:

receive, a plurality of Electrophysiology (EP) signals from a heart surface model as an input, wherein each Electrophysiology (EP) signal from the plurality of Electrophysiology (EP) signals corresponds to cardiac transmembrane potential (TMP) giving rise to cardiac contraction, wherein the cardiac transmembrane potential (TMP) of the heart surface model is determined through a contractility function and wherein the contractility function determines a compliance function of auricles and ventricles;

generate, by a cardiac source module, a Forward Electrophysiology signal from the plurality of Electrophysiology (EP) signals;

process, the Forward Electrophysiology signal, to generate a single lead ECG template, wherein the single lead ECG template comprises at least one of a characteristic constituent comprising: (i) a auricular depolarization (PQ) segment, (ii) a ventricular depolarization (QRS) segment, (iii) a ventricular repolarization (ST) segment and combination thereof, wherein to generate the single lead ECG template, the cardiac source module is expressed as equivalent double layer of sources on closed surface of atrium and ventricles, wherein the single lead ECG template is generated based on a biophysical model that connects the cardiac transmembrane potential (TMP) of representative myocytes on the heart surface model to an electrocardiogram (ECG) signal on surface of a body, and wherein the generated single lead ECG template serves as a driving signal to a hemodynamic module;

estimate, by the hemodynamic module, a plurality of hemodynamic parameters based on the single lead ECG template, wherein the plurality of hemodynamic parameters comprises a left heart atrium compliance function $C_{la}(t)$ and a left heart ventricle compliance function $C_{lv}(t)$, wherein the left heart atrium compliance function $C_{la}(t)$ is computed based on at least one of (i) a minimum value of the left heart atrium, (ii) a maximum value of the left heart atrium, (iii) a left heart atrium activation function ($A_{la}$) is computed based on left heart atrium activation time analogous to the auricular depolarization (PQ) segment and the time duration of the cardiac cycle, and (iv) a time delay in firing between the left heart atrium and the left heart ventricle, wherein the left heart ventricle activation function ($A_{lv}(t)$) is computed based on systolic and diastolic time duration of the cardiac cycle analogous to (i) the ventricular depolarization (QRS) segment, and (ii) the ventricular repolarization (ST) segment and wherein the left heart ventricle compliance function $C_{lv}(t)$ is computed based on an end systolic compliance and the left heart ventricle activation function ($A_{lv}(t)$);

estimate, a plurality of cardiac pressure-volume loop variables based on atleast one of (i) the plurality of hemodynamic parameters, and (ii) pressure variation associated with cardiac excitation, and wherein the plurality of cardiac pressure-volume loop variables includes at least one of (i) a dynamic change observed in a systemic artery pressure is estimated based on at least one of (i) a systemic artery compliance, (ii) the left heart ventricle pressure, (iii) a systemic ventricle pressure, (iv) a systemic artery pressure, (v) a resistance value observed in systemic vessels, and (vi) a resistance value observed in aortic vessel, (ii) a dynamic change observed in a left heart ventricle pressure is estimated based on at least one of (i) the left heart ventricle compliance function, (ii) the left heart ventricle pressure, (iii) a pulmonary vein pressure, (iv) the systemic artery pressure, (v) a resistance value observed in mitral vessel, and (vi) a resistance value observed in aortic vessel and (iii) a dynamic change observed in a right ventricle pressure is estimated based on at least one of (i) the right heart ventricle compliance function, (ii) a systemic vein pressure, (iii) the right heart ventricle pressure, (iv) a resistance value observed in tricuspid vessel, (v) a pulmonary artery pressure, and (vi) a resistance value observed in pulmonary valve; and determine, myocardial ischemia severity of the heart surface model based on (i) a scar tissue size, (ii) a velocity reduction value of the cardiac affected region, (iii) the transmembrane potential (TMP) amplitude and repolarization time, (iv) the single lead ECG template and (v) the plurality of cardiac pressure-volume loop variables, wherein the myocardial ischemia severity includes one of moderate ischemia, severe ischemia and silent ischemia, thereby facilitating in generation of synthetic data for disease classification pertaining to a coronary artery.

7. One or more non-transitory machine-readable information storage mediums comprising one or more instructions which when executed by one or more hardware processors perform actions comprising:

receive, a plurality of Electrophysiology (EP) signals from a heart surface model as an input, wherein each Electrophysiology (EP) signal from the plurality of Electrophysiology (EP) signals corresponds to cardiac transmembrane potential (TMP) giving rise to cardiac contraction, wherein the cardiac transmembrane potential (TMP) of the heart surface model is determined through a contractility function and wherein the contractility function determines a compliance function of auricles and ventricles;

generate, by a cardiac source module, a Forward Electrophysiology signal from the plurality of Electrophysiology (EP) signals;

process, the Forward Electrophysiology signal, to generate a single lead ECG template, wherein the single lead ECG template comprises at least one of a characteristic constituent comprising: (i) a auricular depolarization (PQ) segment, (ii) a ventricular depolarization (QRS) segment, (iii) a ventricular repolarization (ST) segment and combination thereof, wherein to generate the single lead ECG template, the cardiac source module is expressed as equivalent double layer of sources on closed surface of atrium and ventricles, wherein the single lead ECG template is generated based on a biophysical model that connects the cardiac transmembrane potential (TMP) of representative myocytes on the heart surface model to an electrocardiogram (ECG) signal on surface of a body, and wherein the generated single lead ECG template serves as a driving signal to a hemodynamic module;

estimate, by the hemodynamic module, a plurality of hemodynamic parameters based on the single lead ECG template, wherein the plurality of hemodynamic parameters comprises a left heart atrium compliance function $C_{la}(t)$ and a left heart ventricle compliance function $C_{lv}(t)$, wherein the left heart atrium compliance function $C_{la}(t)$ is computed based on at least one of (i) a minimum value of the left heart atrium, (ii) a maximum value of the left heart atrium, (iii) a left heart atrium activation function ($A_{la}$), and (iv) a time delay in firing between the left heart atrium and the left heart ventricle, wherein the left heart ventricle activation function ($A_{lv}(t)$) is computed based on systolic and diastolic time duration of the cardiac cycle analogous to (i) the ventricular depolarization (QRS) segment, and (ii) the ventricular repolarization (ST) segment and wherein the left heart ventricle compliance function $C_{lv}(t)$ is computed based on an end systolic compliance and the left heart ventricle activation function ($A_{lv}(t)$);

estimate, a plurality of cardiac pressure-volume loop variables based on atleast one of (i) the plurality of hemodynamic parameters, and (ii) pressure variation associated with cardiac excitation, and wherein the plurality of cardiac pressure-volume loop variables includes at least one of (i) a dynamic change observed in a systemic artery pressure is estimated based on at least one of (i) a systemic artery compliance, (ii) the left heart ventricle pressure, (iii) a systemic ventricle pressure, (iv) a systemic artery pressure, (v) a resistance value observed in systemic vessels, and (vi) a resistance value observed in aortic vessel, (ii) a dynamic change observed in a left heart ventricle pressure is estimated based on at least one of (i) the left heart ventricle compliance function, (ii) the left heart ventricle pressure, (iii) a pulmonary vein pressure, (iv) the systemic artery pressure, (v) a resistance value observed in mitral vessel, and (vi) a resistance value observed in aortic vessel and (iii) a dynamic change observed in a right ventricle pressure is estimated based on at least one of (i) the right heart ventricle compliance function, (ii) a systemic vein pressure, (iii) the right heart ventricle pressure, (iv) a resistance value observed in tricuspid vessel, (v) a pulmonary artery pressure, and (vi) a resistance value observed in pulmonary valve; and determine, myocardial ischemia severity of the heart surface model based on (i) a scar tissue size, (ii) a velocity reduction value of the cardiac affected region, (iii) the transmembrane potential (TMP) amplitude and repolarization time, (iv) the single lead ECG template and (v) the plurality of cardiac pressure-volume loop variables, wherein the myocardial ischemia severity includes one of moderate ischemia, severe ischemia and silent ischemia, thereby facilitating in generation of synthetic data for disease classification pertaining to a coronary artery.

* * * * *